United States Patent [19]

Batalin et al.

[11] 4,298,503

[45] Nov. 3, 1981

[54] METHOD OF PREPARING CALCIUM BORON PHOSPHATE CATALYST

[76] Inventors: Oleg E. Batalin, ulitsa Ordzhonikidze, 45, kv. 85; Arkady S. Dykman, ulitsa Leni Golikova, 37, korpus 4, kv. 15; Alexandr I. Osadchenko, ulitsa Sofiiskaya, 23, korpus 2, kv. 174; Galina F. Balkhanova, ulitsa Telmana, 48, korpus 3, kv. 60, all of Leningrad; Izrail M. Belgorodsky, Molodezhny bulvar, 50, kv. 25, Tolyatti; Vladimir I. Nevstruev, ulitsa Karla Marxa, 52, kv. 31, Tolyatti; Valery A. Radionov, ulitsa Matrosova, 30, kv. 180, Tolyatti; Eduard A. Tulchinsky, ulitsa Ushakova, 46, kv. 12, Tolyatti; Valentin M. Belyaev, prospekt Lenina, 32, kv. 20, Volzhsky; Jury I. Smolin, ulitsa Lenina, 97, kv. 494, Volzhsky; Mark I. Breiman, ulitsa Chaikovskogo, 17, kv. 12, Volzhsky; Vitaly V. Orlyansky, ulitsa Pionerskaya, 8a, kv. 4, Volzhsky; Nikolai Y. Zhirnov, ulitsa Sovetskaya, 59, kv. 35, Volzhsky; Nikolai V. Galibin, ulitsa Pushkina, 122, kv. 49, Volzhsky; Adrian P. Troitsky, ulitsa Miklukho-Maklaya, 65, korpus 2, kv. 48, Moscow; Vladimir V. Kovalenko, ulitsa Tsiolkovskogo, 7/2, kv. 38, Voronezh, all of U.S.S.R.

[21] Appl. No.: 133,647

[22] Filed: Mar. 24, 1980

[51] Int. Cl.³ .................... B01J 37/02; B01J 21/02
[52] U.S. Cl. .................................. 252/432; 252/437
[58] Field of Search ............... 423/313, 277; 252/432, 252/437

[56] References Cited

U.S. PATENT DOCUMENTS

| | | | |
|---|---|---|---|
| 2,232,610 | 2/1941 | Joshua et al. | 252/432 |
| 3,632,575 | 1/1972 | Mansmann et al. | 252/432 |
| 3,872,216 | 3/1975 | Kachalova et al. | 423/318 |
| 4,025,566 | 5/1977 | Nagai et al. | 252/432 X |

*Primary Examiner*—G. O. Peters
*Attorney, Agent, or Firm*—Steinberg & Raskin

[57] ABSTRACT

The invention relates to a method of preparing a calcium boron phosphate catalyst, comprising the steps of reacting calcium salts with phosphoric acid salts in aqueous ammonia, separating the resulting precipitate from the reaction mixture thus obtained, suitably shaping said precipitate, drying it, and heat treating at an elevated temperature in the presence of steam or steam with an inert gas, mixed with at least one of the components selected from the group consisting of boric acid and, a mixture of boric and phosphoric acids, the molar ratio of boric to phosphoric acids being between 1.0:1 and 10:1.

The reaction of calcium salts with phosphoric acid salts in aqueous ammonia is effected with the starting reactants taken in the molar ratio of 1.5:1 if no phosphoric acid treatment is used, or with the starting reactants in a molar ratio of between 1.5:1 to 5.0:1 if the reaction mixture is treated with a phosphoric acid solution to pH of from 5.0 to 7.0.

8 Claims, No Drawings

METHOD OF PREPARING CALCIUM BORON PHOSPHATE CATALYST

FIELD OF THE INVENTION

The present invention relates to the production of catalysts such as can be used, for example, in the manufacture of isoprene from isobutylene and formaldehyde, and more particularly to a method of preparing a calcium boron phosphate catalyst usable for the decomposition into isoprene of 1,3-dioxanes and, in particular, 4,4-dimethyl-1,3-dioxane (hereinafter referred to as DMD), as well as for the alcohol dehydration reactions.

BACKGROUND OF THE INVENTION

It has been known in the prior art to prepare phosphates of metals of Group II of the Periodic Table, usable as catalysts for selective cleavage of $\rightarrow$C—O- bonds in organic compounds, and, specifically, for converting 4,4-dimethyl-1,3-dioxane into isoprene, as well as for dehydration of alcohols, by precipitating tertiary phosphates of Group II metals from aqueous solutions of their salts taken in conjunction with water-soluble salts of phosphoric acid, followed by separating the precipitate, washing the paste obtained, and shaping it into catalyst granules (cf U.S. Pat. No. 3,872,216).

Catalysts prepared by the above technique, however, are characterized by low selectivity, equal to 78 to 82 mole %, low activity resulting in DMD space velocities as low as 0.7 $h^{-1}$, and high operating temperatures equal to about 375° C.

Selectivity is defined herein as the ratio of the amount in moles of isoprene formed to the amount in moles of DMD converted. Selectivity is expressed in percent.

Selectivity is quantitatively depedent upon catalyst composition and structure, as well as upon the process conditions under which the catalyst operates.

Increased selectivity will lead to reduced DMD consumption rates per unit of finished product. The relatively low selectivity of the catalyst obtainable by the aforesaid prior-art technique would result in high feedstock consumption rates in isoprene production, varying between ca. 2.10 and 2.25 kg of DMD per 1 kg of isoprene.

The activity of catalysts is dependent upon their acidity which is determined by the number and efficiency of the active centres and can be characterized by the DMD conversion degree.

DMD conversion degree is defined herein as the ratio of the amounts of DMD converted to DMD used, expressed in percent.

Known in the art is a method of preparing calcium phosphate catalysts, comprising the steps of reacting calcium salts with phosphoric acid salts in aqueous ammonia, followed by separating the resulting precipitate from the reaction mixture, washing, drying and heat treating it with the use of superheated steam or a mixture of steam and air at high temperatures (cf U.S. Pat. No. 3,846,338).

The catalysts obtained by this prior art technique are relatively low in activity.

Furthermore, calcium phosphate catalysts prepared by said technique are lacking in efficiency, which is as low as 0.3 to 0.4 ton/h of iosprene per cubic meter of catalyst.

The efficiency of a catalyst depends on its activity and selectivity, as well as on the feedstock space velocity.

In the prior-art technique, heat treatment of the catalyst is carried out at high temperatures, which involves overheating of the heat carrier to temperatures as high as 650° to 800° C. and high process power inputs, as well as the use of special heat-resistant materials for the reactors adapted to produce the catalyst.

Furthermore, the catalyst obtained by the aforesaid technique has a relatively short useful life of 250 hours.

The catalyst life depends on many factors including catalyst composition and structure, catalyst activity, operating temperatures, and coke deposition. Coke deposition is understood to denote coke depositing on the catalyst in the process of DMD decomposition. It is determinable as the ratio of the amount in moles of coke deposited to the amount in moles of DMD converted, expressed in percent.

In spite of the advantages inherent in the prior-art techniques for preparation of calcium phosphate catalysts, no commercial process for converting DMD into isoprene based thereon has been developed so far, since there is no catalyst as yet with selectivity and stability such as to permit a commercial process with a high yield of the desired product.

SUMMARY OF THE INVENTION

It is an object of the present invention to provide a method of preparing a high-activity calcium boron phosphate catalyst usable at lower operating temperatures, lower than or equal to 300° C.

Another object of the present invention is to provide a method of preparing a calcium boron phosphate catalyst that would yield a catalyst with good stability at low operating temperature.

A further object of the invention is to provide a method of preparing a high-efficiency calcium boron catalyst.

A still further object of this invention is to provide a method of preparing a high-selectivity calcium boron phosphate catalyst.

With these and other objects in view, there is provided a method of preparing a calcium boron phosphate catalyst, comprising the steps of reacting calcium salts with phosphoric acid salts in aqueous ammonia, separating the resulting precipitate from the reaction mixture, suitably shaping said precipitate, drying it, and heat treating at an elevated temperature in the presence of steam, or a mixture of steam and an inert gas, in which method, according to the invention, heat treatment is carried out in the presence of steam mixed with boric acid or boric and phosphoric acids.

The heat treatment thus performed yields a calcium boron phosphate catalyst with good stability at low operating temperatures less than or equal to 300° C.

It is advisable that the heat treatment procedure be carried out in the presence of 0.01 to 0.8% by mass of boric acid, this permitting a calcium boron phosphate catalyst featuring high activity at low operating temperatures.

The heat treatment procedure is preferably to be in the presence of boric acid taken in the amount of 0.02% by mass.

The best results can be achieved with the heat treatment, carried out using boric acid in the aforesaid amount.

It is also advisable that heat treatment be carried out using boric and phosphoric acids in a molar ratio of between 0.1:1 and 10:1.

Using boric and phosphoric acids in the above range of molar ratios results in enhanced stability of calcium boron phosphate catalysts.

It is desirable that heat treatment be carried out with boric and phosphoric acids taken in an equimolar ratio.

An equimolar ratio of boric and phosphoric acids can give the best results in so far as stability is concerned.

The reaction of calcium salts with phosphoric acid salts is preferably carried out in aqueous ammonia with the starting reactants taken in the molar ratio of 1.5:1.

Reacting the above components under conditions as described above will yield a calcium boron phosphate catalyst featuring low coke deposition characteristics.

It is also advisable that the reaction of calcium salts with phosphoric acid salts in aqueous ammonia be carried out with the starting reactants taken in a molar ratio of between 1.5:1 and 5:1, and the resultant reaction mixture be treated with a phosphoric acid solution to pH of from 5.0 to 7.0.

The range of molar ratios for the starting reactants and the pH range of the reaction mixture as specified above are consistant with obtaining a calcium boron phosphate catalyst of desired structure and composition.

The reaction mixture is preferably to be treated with a phosphoric acid solution to pH of from 5.5 to 6.0.

With the proposed method, a catalyst can be obtained featuring high selectivity (87.2 to 88 mole %), high activity at low operating temperatures lower than or equal to 300° C., low coke deposition, and high stability. The DMD conversion remains practically invariant during 100 hours of operation.

The aforesaid and other objects and additional features of the present invention are set forth in the appended claims, and the present invention will be more fully apparent from the detailed description of embodiments thereof presented hereinunder.

DETAILED DESCRIPTION OF THE EMBODIMENTS

The proposed method of preparing a calcium boron phosphate catalyst can be realized as follows.

The starting reactants to be used are solutions of calcium salts such as calcium chloride and those of phosphoric acid salts such as diammonium phosphate, disodium phosphate, etc. A suitable amount of ammonia solution is added to the phosphoric acid salt solution before reacting it with the calcium salt solution for pH control of the medium.

The solutions of calcium and phosphoric acid salts are gradually introduced into a vessel fitted with a stirrer, with the resulting slurry being continuously stirred. The reaction is carried out with the calcium salts and phosphoric acid salts taken in the molar ratio of 1.5:1. However the reaction is realizable with the starting reactants having a molar ratio anywhere within the range of 1.5:1 to 5.0:1, preferably 2.5:1. In cases such as these the reaction mixture formed is to be treated with a phosphoric acid solution to pH of from 5.0 to 7.0, preferably to pH of from 5.5 to 6.0.

The range of molar ratios for calcium salts and phosphoric acid salts and the pH range of the reaction mixture as specified above are consistant with producing catalysts of desired structure and composition.

The resulting precipitate is separated by filtration or any other conventional technique, washed with distilled water to remove calcium salt anions, shaped into granules by a suitable conventional technique, and dried at a temperature between 110° and 140° C. to obtain a raw calcium phosphate which is then loaded into a reactor for further treatment.

The reactor is a quartz tube of 20 to 26 mm in diameter, and is placed into an electrically heated oven for the catalyst enclosed in the reactor to undergo heat treatment at a temperature of between 400° and 600° C., using steam with boric acid or with boric and phosphoric acids.

Where a calcium boron phosphate catalyst is obtained without pretreatment of the reaction mixture with phosphoric acid solution, heat treatment is preferably performed at 400° C.

However, when the process of calcium boron phosphate catalyst preparation comprises the step of treating the slurry with phosphoric acids to provide the pH value of the reaction mixture within the range of 5.0 to 7.0, the heat treatment temperature should preferably be 450° C.

Heat treatment can also be carried out using steam mixed with an inert gas such as nitrogen, argon, etc.

Steam is fed in at a space velocity of 1.0 to 2.0 h$^{-1}$. Boric acid content in the steam is 0.01 to 0.8% by mass, preferably 0.02% by mass.

When the catalyst heat treatment is performed in the presence of a mixture of boric and phosphoric acids, the boric acid content in the steam ranges from 0.001 to 0.02% by mass and that of phosphoric acid 0.0015 to 0.03% by mass, preferably 0.002% by mass of boric acid and 0.003% by mass of phosphoric acid.

In the course of heat treatment the molar ratio of boric to phosphoric acids is maintained within 0.1:1 to 10:1, preferably at 1:1.

Heat treatment times are within 2 to 50 hours, preferably between 20 and 30 hours.

The calcium boron phosphate catalyst thus obtained has the following characteristics: DMD conversion over 100 operating hours being substantially constant (ca. 90%), selectivity 87.2 to 88 mole %, coke deposition below 1 mole %.

The following typical examples will further illustrate certain aspects of the present invention, delineating more clearly the features and advantages specific to it.

EXAMPLE 1

The starting reactants used for the preparation of a raw calcium phosphate catalyst are 1.78 l of an aqueous calcium chloride solution containing 101.892 g of calcium chloride per 1 l of the solution, and 1.608 l of an aqueous diammonium phosphate solution containing 51.08 g of diammonium phosphate per 1 l of the solution. An ammonia solution with a concentration of 152.15 g/l is added to the diammonium phosphate solution on the basis of having 2.33 moles of ammonia per 1 mole of diammonium phosphate.

The starting reactants are gradually poured into a vessel fitted with a stirrer, the molar ratio of calcium chloride to diammonium phosphate being kept at 2.5:1. The pouring procedure continues for 2 hours, the resulting reaction mixture in the form of a slurry being continuously stirred all the while. The pH value of the slurry is found to be 9.0±0.05. The slurry is treated with 150 ml of phosphoric acid concentrated to 281.26 g/l, in order to reduce the pH value to 5.75. The resulting precipitate is separated from the reaction mixture by filtration, washed with distilled water to remove chlorine ions, shaped into granules in a press, and dried at 120° C.

The raw calcium phosphate catalyst thus obtained is loaded, in an amount of 24 cm³, into a reactor which has the form of a quartz tube of 20 to 26 mm in diameter. The reactor is placed into an electrically heated oven, and steam mixed with 0.01% by mass of boric acid is used for heat treatment of the raw calcium phosphate catalyst at 450° C. for 20 hours.

The catalyst thus prepared is test run in a DMD decomposition reaction in an atmosphere of steam, followed by regeneration which consists in burning out the coke deposit after every 2 hours of catalyst operation.

The DMD decomposition reaction is carried out at atmospheric pressure and at an average temperature of 280° C. for the duration of 2 hours. DMD is fed in at the rate of 24 cm³/h, and water, at 48 cm³/h, which gives a DMD space velocity of 1.0 $h^{-1}$ and a DMD to steam dilution ratio of 1:2.

The DMD decomposition cycle is followed up by a regeneration cycle using a temperature of 425° C. and feed rates of 48 cm³/h for water and 16.800 cm³/h for air. The duration of the test is 100 hours.

The products of the reaction are analysed using gas-liquid chromatography techniques. The quantity of coke deposited is determined by a conventional method.

The catalyst test results are presented below in Table 1.

EXAMPLE 2

The procedure used to prepare the raw calcium phosphate catalyst is the same as described in Example 1.

The calcium phosphate catalyst thus obtained is subjected to heat treatment at 450° C. for 20 hours with the use of steam mixed with 0.8% by mass of boric acid. The calcium boron phosphate catalyst so prepared is test run as described in Example 1.

The catalyst test results are presented below in Table 1.

EXAMPLE 3

The procedure used to prepare the raw calcium phosphate catalyst is the same as described in Example 1.

Heat treatment of the raw calcium phosphate catalyst thus obtained is performed using steam mixed with 0.02% by mass of boric acid, at 450° C., for 20 hours.

The resulting calcium boron phosphate catalyst is test run as described in Example 1.

The catalyst test results are presented below in Table 1.

EXAMPLE 4

The procedure used to prepare the raw calcium phosphate catalyst is the same as described in Example 1.

Heat treatment of the raw calcium phosphate catalyst thus obtained is performed at 450° C. for 20 hours, using steam mixed with 0.02% by mass of boric acid and 4800 cm³/h of nitrogen, equivalent to a nitrogen space velocity of 200 $h^{-1}$.

The resulting calcium boron phosphate catalyst is test run as described in Example 1.

The catalyst test results are presented below in Table 1.

EXAMPLE 5

The procedure used to prepare the raw calcium phosphate catalyst is the same as described in Example 1. Heat treatment of the raw calcium phosphate thus obtained is carried out at 450° C. for 20 hours, using steam mixed with 0.02% by mass of boric acid and 4800 cm³/h of air, equivalent to an air space velocity of 200 $h^{-1}$.

The resulting calcium boron phosphate catalyst is test run as described in Example 1.

The catalyst test results are presented below in Table 1.

EXAMPLE 6

The procedure used to prepare the raw calcium phosphate catalyst is the same as described in Example 1. Heat treatment of the raw calcium phosphate catalyst thus obtained is carried out at 400° C. for 20 hours, using steam mixed with 0.02% by mass of boric acid.

The resulting calcium boron phosphate catalyst is test run as described in Example 1.

The catalyst test results are presented below in Table 1.

EXAMPLE 7

The procedure used to prepare the raw calcium phosphate catalyst is the same as described in Example 1. Heat treatment of the raw calcium phosphate catalyst thus obtained is carried out at 600° C. for 20 hours, using steam mixed with 0.02% by mass of boric acid.

The resulting calcium boron phosphate catalyst is test run as described in Example 1.

The catalyst test results are presented below in Table 1.

EXAMPLE 8

The procedure used to prepare the raw calcium phosphate catalyst is the same as described in Example 1. Heat treatment of the raw calcium phosphate catalyst thus obtained is performed at 450° C. for 20 hours, using steam mixed with 0.002% by mass of boric acid and 0.003% by mass of phosphoric acid.

The resulting calcium boron phosphate catalyst is test run as described in Example 1.

The catalyst test results are presented below in Table 1.

EXAMPLE 9

The procedure used to prepare the raw calcium phosphate catalyst is the same as described in Example 1. Heat treatment of the raw calcium phosphate catalyst thus obtained is performed at 400° C. for 20 hours, using steam mixed with 0.002% by mass of boric acid and 0.003% by mass of phosphoric acid.

The resulting calcium boron phosphate catalyst is test run as described in Example 1.

The catalyst test results are presented below in Table 1.

EXAMPLE 10

The procedure used to prepare the raw calcium phosphate catalyst is the same as described in Example 1. Heat treatment of the raw calcium phosphate catalyst thus obtained is carried out at 600° C. for 20 hours, using water steam mixed with 0.002% by mass of boric acid and 0.003% by mass of phosphoric acid.

The resulting calcium boron phosphate catalyst is test run as described in Example 1.

The catalyst test results are presented below in Table 1.

EXAMPLE 11

The procedure used to prepare the raw calcium phosphate catalyst is the same as described in Example 1. Heat treatment of raw calcium phosphate catalyst thus obtained is carried out at 450° C. for 20 hours, using steam mixed with 0.02% by mass of boric acid and 0.003% by mass of phosphoric acid.

The resulting calcium boron phosphate catalyst is test run as described in Example 1.

The catalyst test results are presented below in Table 1.

EXAMPLE 12

The procedure used to prepare the raw calcium phosphate catalyst is the same as described in Example 1. Heat treatment of the raw calcium phosphate catalyst thus obtained is carried out at 450° C. for 20 hours, using steam mixed with 0.002% by mass of boric acid and 0.03% by mass of phosphoric acid.

The resulting calcium boron phosphate catalyst is test run as described in Example 1.

The catalyst test results are presented below in Table 1.

EXAMPLE 13

The procedure used to prepare the raw calcium phosphate catalyst is the same as described in Example 1. Heat treatment of the raw calcium catalyst thus obtained is carried out at 450° C. for 20 hours, using steam mixed with 0.002% by mass of boric acid, 0.003% by mass of phosphoric acid, and 4800 dm$^3$/h of nitrogen, equivalent to a nitrogen space velocity of 200 h$^{-1}$.

The resulting calcium boron phosphate catalyst is test run as described in Example 1.

The catalyst test results are presented below in Table 1.

EXAMPLE 14

The procedure used to prepare the raw calcium phosphate catalyst is the same as described in Example 1. Heat treatment of calcium phosphate catalyst thus obtained is carried out at 450° C. for 20 hours, using steam mixed with 0.002% by mass of boric acid, 0.003% by mass of phosphoric acid, and 4800 cm$^3$/h of air, equivalent to an air space velocity of 200 h$^{-1}$.

The resulting calcium boron phosphate catalyst is test run as described in Example 1.

The catalyst test results are presented below in Table 1.

EXAMPLE 15

The starting reactants used for preparation of a raw calcium phosphate catalyst are 1.18 l of a calcium chloride solution containing 99.8 g/l of calcium chloride and 2.0 l of a disodium phosphate solution containing 50.21 g/l of disodium phospate. An ammonia solution with a concentration of 130 g/l is added to the disodium phosphate solution immediately prior to the reaction, on the basis of having 1.3 moles of ammonia per 1 mole of disodium phosphate. The calcium chloride and disodium phosphate solutions are gradually poured into a vessel fitted with a stirrer. The pouring procedure continues for 2 hours, the resulting slurry being continuously stirred all the while. Reaction is carried out with the solutions used at a constant volume ratio to ensure a calcium chloride to disodium phosphate molar ratio of 1.5:1 and the slurry pH value of 9.0±0.05. The resulting precipitate is separated by filtration, washed with distilled water to remove chlorine ions, shaped into granules, and dried at a temperature of 120° C. Heat treatment of the calcium phosphate obtained is performed at 400° C. for 20 hours, using steam mixed with 0.02% by mass of boric acid.

The calcium boron phosphate catalyst thus obtained is test run as described in Example 1.

The test results for the calcium boron phosphate catalyst are presented below in Table 1.

EXAMPLE 16

The procedure used to prepare the raw calcium phosphate catalyst is the same as described in Example 15.

Heat treatment of the calcium phosphate obtained is carried out at 400° C. for 20 hours, using water vapour mixed with 0.002% by mass of boric acid and with 0.003% by mass of phosphoric acid.

The calcium boron phosphate catalyst thus obtained is test run as described in Example 1.

The test results for the calcium boron phosphate catalyst are presented below in Table 1.

Although the present invention has been described herein with reference to the preferred typical embodiments thereof, it will be apparent to those skilled in the art that there may be minor modifications made in the procedures comprised in the proposed method for preparation of calcium phosphate catalysts without departing from the spirit of the invention.

All such modifications and variations are contemplated to be embraced in the spirit and scope of the invention, as defined in the appended claims.

TABLE 1

Results of Catalyst Testing in DMD Decomposition Runs
Operating temperature: 280° C.
DMD space velocity: 1.0 h$^{-1}$
DMD: H$_2$O dilution ratio: 1:2

| Characteristics | Catalysts as per Example Nos. | | | | | | | | | | | | | | | |
|---|---|---|---|---|---|---|---|---|---|---|---|---|---|---|---|---|
| | 1 | | 2 | | 3 | | 4 | | 5 | | 6 | | 7 | | 8 | |
| Cycle Nos. | 1 | 50 | 1 | 50 | 1 | 50 | 1 | 50 | 1 | 50 | 1 | 50 | 1 | 50 | 1 | 50 |
| DMD conversion, % | 86.9 | 83.0 | 89.9 | 86.0 | 90.0 | 86.3 | 90.1 | 86.2 | 90.2 | 86.3 | 90.1 | 86.3 | 83.0 | 79.6 | 90.1 | 89.8 |
| Selectivity, mole % | 87.3 | 87.6 | 87.3 | 87.6 | 87.4 | 87.7 | 87.3 | 87.7 | 87.3 | 87.7 | 87.2 | 87.6 | 87.5 | 87.5 | 87.8 | 88.0 |
| Coke deposition mole % | 0.77 | 0.61 | 0.97 | 0.67 | 0.93 | 0.64 | 0.99 | 0.63 | 0.98 | 0.62 | 0.99 | 0.66 | 0.48 | 0.36 | 0.72 | 0.54 |

| Characteristics | Catalysts as per Example Nos. / Catalyst as per Example Nos. | | | | | | | | | | | | | | | |
|---|---|---|---|---|---|---|---|---|---|---|---|---|---|---|---|---|
| | 9 | | 10 | | 11 | | 12 | | 13 | | 14 | | 15 | | 16 | |
| Cycle Nos. | 1 | 50 | 1 | 50 | 1 | 50 | 1 | 50 | 1 | 50 | 1 | 50 | 1 | 50 | 1 | 50 |

TABLE 1-continued

Results of Catalyst Testing in DMD Decomposition Runs
Operating temperature: 280° C.
DMD space velocity: 1.0 h$^{-1}$
DMD: H$_2$O dilution ratio: 1:2

| DMD conversion, % | 90.3 | 89.9 | 83.1 | 82.7 | 90.0 | 89.3 | 89.9 | 89.1 | 90.2 | 89.8 | 90.1 | 89.9 | 35.1 | 29.6 | 35.2 | 34.2 |
|---|---|---|---|---|---|---|---|---|---|---|---|---|---|---|---|---|
| Selectivity, mole % | 87.3 | 87.7 | 87.5 | 87.7 | 87.5 | 87.7 | 87.4 | 87.7 | 87.4 | 87.9 | 87.4 | 88.0 | 84.8 | 84.8 | 85.0 | 85.0 |
| Coke deposition mole % | 0.92 | 0.56 | 0.43 | 0.33 | 0.81 | 0.62 | 0.82 | 0.63 | 0.81 | 0.55 | 0.83 | 0.52 | 0.18 | 0.13 | 0.16 | 0.12 |

We claim:

1. Method of preparing a calcium boron phosphate catalyst, which comprises reacting a calcium salt with a phosphoric acid salt in aqueous ammonia, thereby forming a reaction mixture including a precipitate, separating the thus formed precipitate from the reaction mixture, shaping said precipitate to a predetermined shape drying the thus shaped precipitate, and heat treating the shaped, dried precipitate at an elevated temperature in the presence of steam or steam with an inert gas, said steam or steam with inert gas being mixed with at least one of the components selected from the group consisting of boric acid and a mixture of boric and phosphoric acids, thereby forming a shaped calcium boron phosphate catalyst.

2. Method according to claim 1, wherein said heat treatment is carried out with said steam or steam with inert gas mixed with boric acid in an amount of between 0.01 to 0.8% by mass.

3. Method according to claim 2, wherein said heat treatment is carried out with said steam or steam with inert gas mixed with boric acid in the amount of 0.02% by mass.

4. Method according to claim 1, wherein said heat treatment is carried out with said steam or steam with inert gas mixed with boric and phosphoric acids in a molar ratio of between 0.1:1 and 10:1.

5. Method according to claim 4 wherein said boric and phosphoric acids are in equimolar ratio.

6. Method according to claim 1, wherein the reaction of said calcium salt with said phosphoric acid salt in aqueous ammonia is effected with the starting reactants used in the molar ratio of 1.5:1.

7. Method according to claim 1, wherein the reaction of said calcium salt with said phosphoric acid salt in aqueous ammonia is effected with the starting reactants used in a molar ratio of between 1.5:1 and 5.0:1, and wherein the reaction mixture obtained is treated with a solution of phosphoric acid to pH from 5.0 to 7.0.

8. Method according to claim 7, wherein the treatment with the solution of phosphoric acid is to pH of from 5.5 to 6.0.

* * * * *